United States Patent
Rishoni et al.

(10) Patent No.: US 11,883,101 B2
(45) Date of Patent: Jan. 30, 2024

(54) SYSTEM AND METHOD FOR ENABLING COMMUNICATION THROUGH EYE FEEDBACK

(71) Applicant: EYEFREE ASSISTING COMMUNICATION LTD., Tel Aviv (IL)

(72) Inventors: Shay Rishoni, Ramat Hasharon (IL); Tal Kellner, Herzlia (IL); Itai Kornberg, Ramat Gan (IL); Or Retzkin, Tel Aviv (IL)

(73) Assignee: EYEFREE ASSISTING COMMUNICATION LTD., Tel Aviv (IL)

( * ) Notice: Subject to any disclaimer, the term of this patent is extended or adjusted under 35 U.S.C. 154(b) by 538 days.

(21) Appl. No.: 15/557,031

(22) PCT Filed: Mar. 2, 2016

(86) PCT No.: PCT/IL2016/050235
§ 371 (c)(1),
(2) Date: Sep. 8, 2017

(87) PCT Pub. No.: WO2016/142933
PCT Pub. Date: Sep. 15, 2016

(65) Prior Publication Data
US 2020/0022577 A1 Jan. 23, 2020

Related U.S. Application Data

(60) Provisional application No. 62/130,637, filed on Mar. 10, 2015.

(51) Int. Cl.
*G06F 3/01* (2006.01)
*A61B 3/113* (2006.01)
(Continued)

(52) U.S. Cl.
CPC ............ *A61B 3/113* (2013.01); *A61B 3/0008* (2013.01); *A61B 3/032* (2013.01);
(Continued)

(58) Field of Classification Search
CPC . G06F 3/013; G06F 3/017; G06F 3/04; G06F 3/04842; G06F 3/0485;
(Continued)

(56) References Cited

U.S. PATENT DOCUMENTS 4,836,670 A * 6/1989 Hutchinson ............ A61B 3/113
351/210
4,950,069 A * 8/1990 Hutchinson ............ A61B 3/113
351/210
(Continued)

FOREIGN PATENT DOCUMENTS

CN 101893934 11/2010
JP 0749744 A 2/1995
(Continued)

OTHER PUBLICATIONS

English translation of KR-20130043369-A, espacenet, retrieved Jun. 3, 2021 (Year: 2021).*
(Continued)

*Primary Examiner* — Christopher Stanford
(74) *Attorney, Agent, or Firm* — XSENSUS LLP

(57) ABSTRACT

System and method for enabling user communication with eye-based feedback. A selection interface selectively presents a series of communication options to the user. A sensor detects light reflected from the eye of the user and provides a correlative signal, which is processed to determine a relative eye orientation that includes the relative orientation of the pupil with respect to the head orientation of the user. The eye may be illuminated by a light source or ambient lighting. The sensor may detect infrared light reflected from
(Continued)

the eye illuminated by an infrared light source. The relative eye orientation may be determined by processing images captured by an image sensor. The relative eye orientation may be determined by detecting an instantaneous relative orientation of the pupil or by detecting a transient change of the pupil. Based on the determined relative eye orientation, a selected communication option is determined and implemented.

20 Claims, 7 Drawing Sheets

(51) Int. Cl.
  *A61B 3/00* (2006.01)
  *A61B 3/032* (2006.01)
  *G02B 27/00* (2006.01)
  *G02B 27/01* (2006.01)
  *G06F 3/0482* (2013.01)

(52) U.S. Cl.
  CPC ..... *G02B 27/0093* (2013.01); *G02B 27/0172* (2013.01); *G06F 3/013* (2013.01); *G06F 3/017* (2013.01); *G06F 3/0482* (2013.01); *G02B 2027/0138* (2013.01)

(58) Field of Classification Search
  CPC ............ A61B 3/113; G02B 2027/0138; G02B 2027/014; G02B 2027/0187; G02B 27/0093
  See application file for complete search history.

(56) References Cited

U.S. PATENT DOCUMENTS

| | | | | |
|---|---|---|---|---|
| 4,973,149 A * | 11/1990 | Hutchinson | ............ | A61B 3/113 351/210 |
| 5,912,721 A * | 6/1999 | Yamaguchi | .......... | G06K 9/0061 351/209 |
| 6,421,064 B1 * | 7/2002 | Lemelson | ............... | G06F 3/013 345/688 |
| 6,456,262 B1 * | 9/2002 | Bell | ........................ | A61B 3/113 345/472 |
| 6,943,754 B2 * | 9/2005 | Aughey | ................. | A61B 3/113 345/7 |
| 7,766,479 B2 * | 8/2010 | Ebisawa | ................. | G06F 3/013 351/209 |
| 8,120,577 B2 * | 2/2012 | Bouvin | ............... | G06F 3/04812 345/157 |
| 8,360,578 B2 * | 1/2013 | Nummela | .............. | A61B 3/113 351/209 |
| 8,593,375 B2 | 11/2013 | Maltz | | |
| 8,888,287 B2 * | 11/2014 | Yahav | .................... | G02B 27/01 351/210 |
| 8,955,973 B2 * | 2/2015 | Raffle | .................... | A61B 3/113 351/209 |
| 9,171,198 B1 * | 10/2015 | Raffle | .................. | G02B 27/017 |
| 9,779,478 B1 * | 10/2017 | Wilson | .................. | G06T 3/4092 |
| 10,976,813 B2 * | 4/2021 | Nistico | ................ | G06K 9/0061 |
| 2005/0045373 A1 | 3/2005 | Born | | |
| 2006/0061544 A1 | 3/2006 | Min et al. | | |
| 2010/0125816 A1 | 5/2010 | Bezos | | |
| 2010/0149073 A1 * | 6/2010 | Chaum | .............. | G02B 27/0172 345/8 |
| 2013/0021373 A1 | 1/2013 | Vaught et al. | | |
| 2013/0235347 A1 * | 9/2013 | Hennessey | .............. | G06F 3/013 351/210 |
| 2013/0293488 A1 * | 11/2013 | Na | .......................... | G06F 3/016 345/173 |
| 2013/0307771 A1 * | 11/2013 | Parker | .................. | G06F 3/04842 345/158 |
| 2013/0332827 A1 * | 12/2013 | Smith | .................. | G09B 21/007 715/702 |
| 2014/0026101 A1 * | 1/2014 | Pallakoff | ............... | G06F 3/0483 715/841 |
| 2014/0300535 A1 | 10/2014 | Kim et al. | | |
| 2014/0368442 A1 * | 12/2014 | Vahtola | ................... | G06F 3/013 345/173 |
| 2014/0375541 A1 * | 12/2014 | Nister | .................... | A61B 3/113 345/156 |

FOREIGN PATENT DOCUMENTS

| | | | | |
|---|---|---|---|---|
| JP | 2000137789 | | 5/2000 | |
| JP | 2005100366 A | | 4/2005 | |
| JP | 2006141862 | | 6/2006 | |
| JP | 2007310815 | | 11/2007 | |
| JP | 2007531579 | | 11/2007 | |
| JP | 2012048358 | | 3/2012 | |
| KR | 20130043369 A | * | 4/2013 | |
| KR | 20140132906 | | 11/2014 | |

OTHER PUBLICATIONS

English translation of JP 2007310815, espacenet, retrieved Jun. 3, 2021 (Year: 2021).*

* cited by examiner

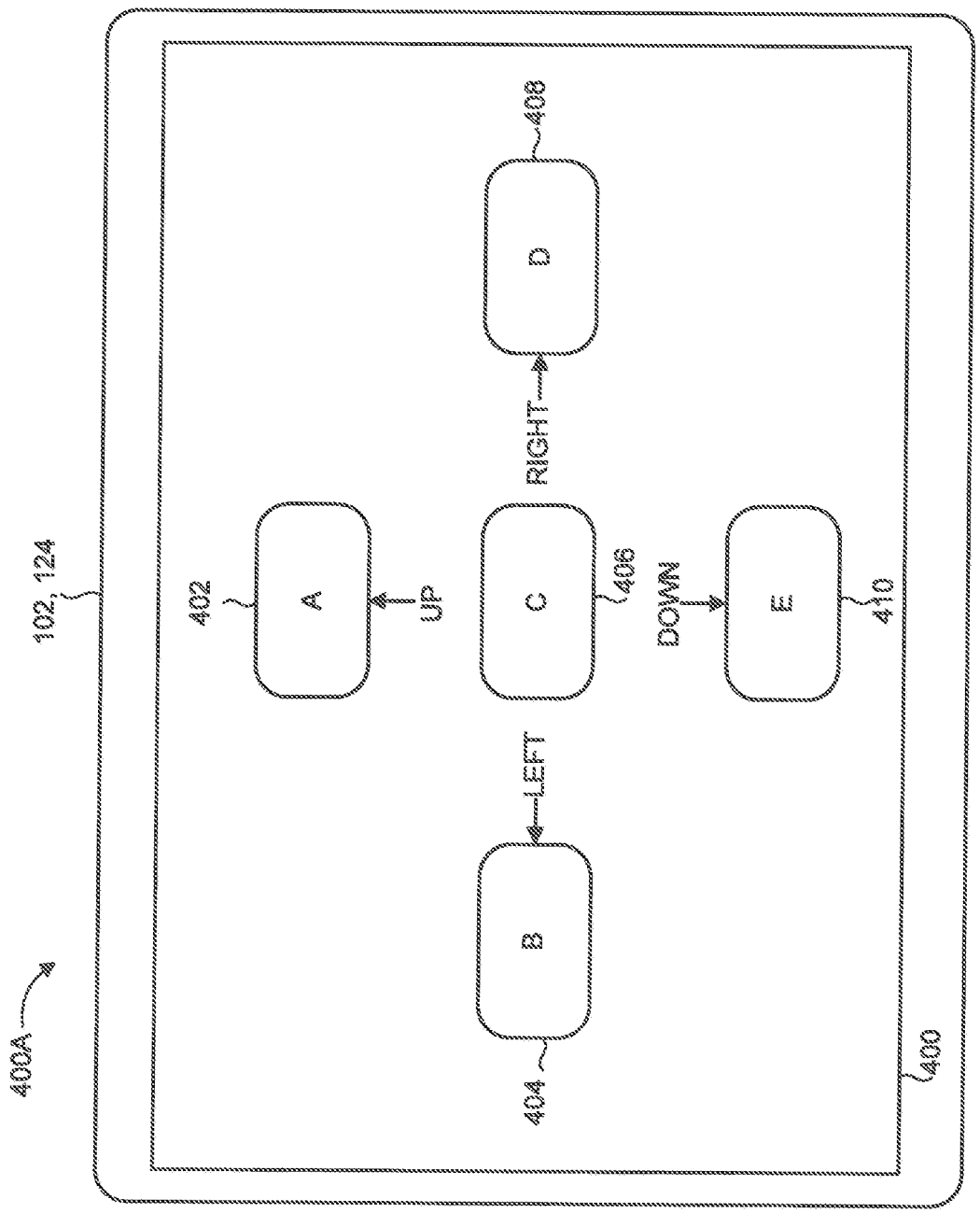

SYSTEM AND METHOD FOR ENABLING COMMUNICATION THROUGH EYE FEEDBACK

FIELD OF THE INVENTION

The present invention relates to eye tracking and to interfaces and user communication platforms.

BACKGROUND OF THE INVENTION

A degenerative disease is characterized by the deterioration of structure or function of body tissue. Degenerative diseases often lead to a loss of control over muscles and a decline of motor function that impair a person's movement capabilities. As a result, the individual may experience severe difficulties or even a complete inability to communicate verbally and/or by using hand motions. Degenerative diseases do not necessarily diminish the person's mind and cognitive function at all or at the same rate as the decline in motor function. In this way, a person with full cognitive activity can lose his ability to interact physically and verbally with his environment. The person's mind can be considered to be essentially trapped or locked into his body.

Some examples of degenerative diseases include: Duchenne muscular dystrophy (DMD), Machado-Joseph disease (MJD), Multiple sclerosis (MS), Muscular dystrophy (MD), Parkinson's and Amyotrophic lateral sclerosis (ALS). Amyotrophic lateral sclerosis (ALS), also known as Lou Gehrig's disease and Charcot disease, is a disorder that involves the death of neurons and is characterized by stiff muscles, muscle twitching, and gradually worsening weakness due to muscle wasting. ALS typically causes difficulty speaking, swallowing, and breathing. ALS patients represent a subgroup of people with fully functional cognitive abilities that gradually lose their speech and the use of their upper limbs.

Aside from those suffering from degenerative diseases, other groups of people may also experience a loss of physical capabilities while retaining their mental capabilities (i.e., have difficulty verbally communicating while maintaining full cognitive capabilities). For example, those suffering from locked-in syndrome (LIS) or neurodegenerative diseases like Parkinson's or Huntington's, stroke and other accident victims (e.g., traffic accidents), patients connected to a respirator (mechanically ventilated patients) who cannot speak due to having a breathing tube inserted in their throat, those too weak or unable to move their limbs, those who are paralyzed, or others who have reached a state that even though their brains are functioning properly they cannot interact with their environment due to technical restrictions. Such individuals are thus severely limited in their ability to communicate with other people in their environment.

It can be seen that for those who are locked-in, communication with their surroundings can become very limited. The inability of the person to communicate easily with their environment can lead to further detachment from their surroundings. This may lead to situations when the patient is distressed and unable to relay their life-threatening predicament (which can endanger the patient's life).

One possible approach is to enable an alternative form of communication for such individuals based on characteristics relating to their eyes. For example, the direction or focus of the person's line of sight may be used to provide instructions or otherwise communicate different types of information to their surroundings. There are tools for aiding such alternative (non-verbal) forms of communication, however they are typically relatively expensive, cumbersome and/or immobile (fixed in place). These tools often require the use of a dedicated computer which the tools are mounted to, and are contingent on the stable posture of the person using the tool. These tools can track eye location relative to a display on a screen and translate eye movements to mimic the operation of a mouse cursor on the screen. Hence the focus of the patient is translated to a geographical location of a pointer (or cursor) and the person can control a computer through his eyes in the same way a mouse would be used. For example, the pupil is identified as a point in space and allows the person to control the computer using their eyes similar to the way they would control a computing mouse. Mouse control is not always accurate and people who are locked in typically do not have freedom of movement of the head with relative ease (for example, because they are attached to a piece of medical equipment, such as a respirator). Since these tools require the exact eye gaze location of the user, they typically necessitate relatively frequent re-calibration of the system with the active participation of the user. The calibration process can require an accurate fixation of the user in front of the screen in multiple positions and can take a relatively long time to perform. The calibration process can also often require third party assistance, which can be costly or inconvenient.

U.S. Pat. No. 8,120,577 to Bouvin et al. entitled "Eye Tracker with Visual Feedback" discloses entry of control commands into a computer in response to eye-tracker detected movement sequences of a point of regard over a graphical display.

US 2013/0293488 to Na et al. entitled "Mobile Terminal and Control Method Thereof" discloses a mobile terminal including a camera configured to capture eye gestures of a user and a controller configured to display an eye tracking mode guide based on the captured eye gestures on a display and to select a particular function included in the eye tracking mode guide based on the captured second eye gesture.

U.S. Pat. No. 8,593,375 to Maltz entitled "Eye Gaze User" discloses a software controlled user interface for an eye gaze controlled device, designed to accommodate angular accuracy versus time averaging tradeoffs for eye gaze direction sensors.

U.S. Pat. No. 8,593,375 to Maltz entitled "Eye Gaze User" discloses a software controlled user interface for an eye gaze controlled device, designed to accommodate angular accuracy versus time averaging tradeoffs for eye gaze direction sensors.

U.S. Pat. No. 6,456,262 to Bell entitled "Microdisplay with Eye Gaze Detection" discloses a microdisplay in which a displayed image element may be selected by gazing upon it.

US 2006/0061544 to Min et al. entitled "Apparatus and Method for Inputting Keys Using Biological Signals in Head Mounted Display Information Terminal" discloses a Head Mounted Display where a user inputs a key selected according to the user's biological signals sensed through a biological signal sensing unit having an EOG (Electrooculogram) input unit and an EMG (Electromyogram) input unit for sensing and receiving the biological signals as key inputs.

An example of a system that is operated using eye tracking is the "EyeWriter™" (notimDossiblelabs.com or http://www.evewriter.org/). The EyeWriter™ was developed for the benefit of graffiti artists suffering from ALS.

SUMMARY OF THE INVENTION

In accordance with one aspect of the present invention, there is thus provided a system for enabling a user to communicate with eye-based feedback. The system includes a relative eye orientation sensor, a selection interface and a processor. The selection interface is configured to selectively present a series of communication options to the user. The relative eye orientation sensor is configured to detect light reflecting from the eye of the user and provide a correlative signal. The processor is communicatively coupled with the relative eye orientation sensor and with the selection interface. The processor is configured to receive and process the correlative signal to determine a relative eye orientation of the user, the relative eye orientation including the relative orientation of at least the pupil of the eye with respect to the head orientation of the user. The processor is further configured to determine a selected communication option based on the determined relative eye orientation, and to provide instructions to implement the selected communication option. The system may further include at least one light source for illuminating the eye of the user. The light source may be an infrared (IR) light source, and the relative eye orientation sensor may detect IR light reflected from the eye. The selection interface may include a visual interface, an audible interface, and/or a tactile interface. The light source and/or the relative orientation sensor may be coupled with a wearable head gear worn by the user. The selection interface may operate on a mobile computing device. The relative eye orientation sensor may include at least one image sensor configured to capture images of the eye of the user, where the processor determines the relative eye orientation by image processing of the captured images. The processor may determine the relative eye orientation by detecting an instantaneous relative orientation of the pupil, or by detecting a transient change of the pupil. The processor may be communicatively coupled wirelessly with the relative eye orientation sensor and/or the selection interface. The communication option may include: an audible alarm, a menu selection, a language selection, a confirmation message, a sentence, a phrase, a word, a syllable, a letter, a mobile computing device activation selection, a visual interface deactivation selection, instruction to send an email/SMS/MMS, and/or instructions to implement a computing application. The visual interface may display at least one communication option by: color-coordination, shape-coordination, and/or symbolic images.

In accordance with another aspect of the present invention, there is thus provided a method for enabling a user to communicate with eye-based feedback. The method includes the procedures of: selectively presenting a series of communication options to the user with a selection interface, and detecting light reflected from the eye of the user and providing a correlative signal with a relative eye orientation sensor. The method further includes the procedure of processing the correlative signal to determine a relative eye orientation of the user, the relative eye orientation including the relative orientation of at least the pupil of the eye with respect to the head orientation of the user. The method further includes the procedures of determining a selected communication option based on the determined relative eye orientation, and providing instructions to implement the selected communication option. The method may further include the procedure of illuminating the eye of the user with at least one light source. The eye may be illuminated with IR light, and the relative eye orientation sensor is configured to detect IR light reflected from the eye. A communication option may be presented by the selection interface visually, audibly, and/or in a tactile manner. The procedure of detecting light reflected from the eye of the user may include capturing images of the eye with at least one image sensor, where the relative eye orientation is determined by image processing of the captured images. The relative eye orientation may be determined by detected an instantaneous relative orientation of the pupil, or by detecting a transient change of the pupil. The communication option may include: an audible alarm, a menu selection, a language selection, a confirmation message, a sentence, a phrase, a word, a syllable, a letter, a mobile computing device activation selection, a visual interface deactivation selection, instruction to send an email/SMS/MMS, and/or instructions to implement a computing application. The method may further include the procedure of performing calibration by: comparing consecutive captured images to detect relative changes of the pupil in the eye; marking the pupil in the captured images to track an area of interest signifying the location of the pupil; setting a reference point as the center of a 2D grid and translating eye movements to coordinates on the grid, when determining that the pupil is at the center of the grid, selecting a reference point for building a reference point coordinate system; and determining the range of motion of the user.

BRIEF DESCRIPTION OF THE DRAWINGS

The present invention will be understood and appreciated more fully from the following detailed description taken in conjunction with the drawings in which:

FIG. 4 is an illustration of a letter sub-menu displayed on the display of FIG. 1;

DETAILED DESCRIPTION OF THE EMBODIMENTS

The present invention overcomes the disadvantages of the prior art by providing a system and method for allowing a user to communicate by means of eye-based feedback. In particular, the user can select communication option presented to him/her via a visual, audio and/or tactical interface by providing instructions using merely the relative orientation of his/her eyes to indicate a general direction that he/she is looking. The system determines the relative eye orientation of the user, representing the orientation of the pupil relative to the eye socket or head orientation, by detecting reflections of infrared light (or other light) from the eye, such as by using an IR light source and IR camera or other sensor. The present invention thus allows for improving the quality of life of individuals characterized by a difficulty or inability to communicate verbally and/or manually (e.g., sufferers of locked-in syndrome, such as ALS patients), while maintaining their cognitive awareness, by providing an elegant, accessible, relatively non-expensive, mobile, alternative form of communication. In addition, the system allows for communication and operation of devices while the user is otherwise engaged.

Figure 1:
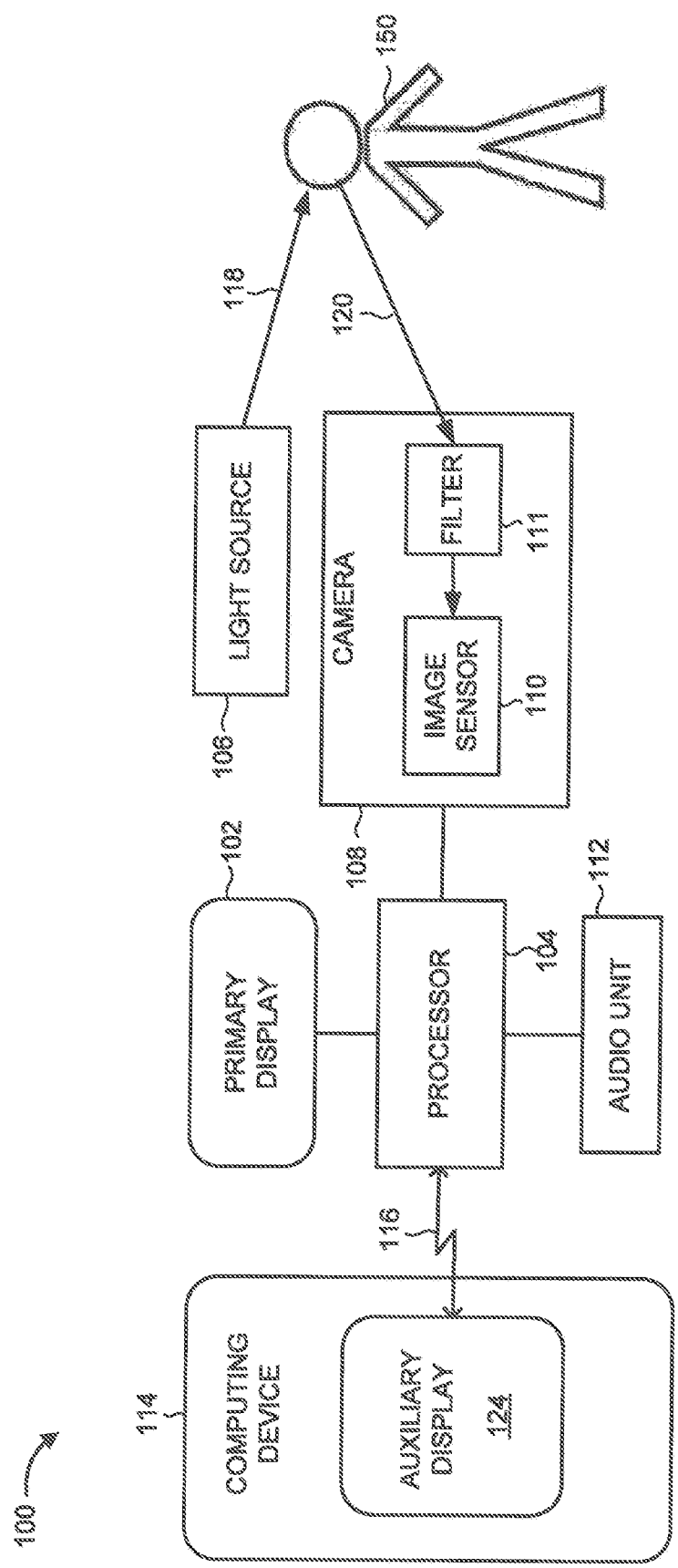
FIG. 1 is a schematic illustration of a system for enabling a user to communicate with eye-based feedback, constructed and operative in accordance with an embodiment of the present invention.

Reference is now made to FIG. 1, which is a schematic illustration of a system, generally referenced 100, for enabling a user to communicate with eye-based feedback, constructed and operative in accordance with an embodiment of the present invention. System 100 includes a primary display 102, an image processor 104, a light source 106, a camera 108 with an image sensor 110 and filter 111, at least one audio unit 112 and a computing device 114 with an auxiliary display 124. Processor 104 is communicatively coupled with primary display 102, with camera 108, with audio unit 112, and with computing device 114. computing device 114 may be communicatively coupled with processor 104 through a wired or wireless communication link 116 (e.g., a two-way Bluetooth connection).

Light source 106 is configured to emit light 118 to illuminate at least one eye of user 150. Light source 106 may be configured to emit non-visible light, such as light in the infrared (IR) spectrum. IR light is particularly desirable because it can be used effectively even in dark rooms with poor lighting conditions, and allows for effective illumination of the eye. Alternatively, other light wavelengths (non-IR light) may be used to illuminate the eye of user 150. Light source 106 typically emits eye-safe light (e.g., in the visible or infrared wavelengths). Eye-safe light can pass through the various optical elements of system 100 in the desired optical path (i.e., transmitted through or reflected from the optical elements in the desired directions), without interfering with the visible light path of the displayed image. As an example, light source 106 can be embodied by four IR LED lights that are arranged in an array (e.g., in a square pattern with each one of the LEDs in a respective corner of the square). Alternatively, light source 106 may be embodied by ambient light, such as solar radiation or indoor lighting.

Camera 108 is configured to capture images of at least one eye of user 150. The line of sight (LOS) of camera 108 is aligned toward the general direction of the face of user 150 The field of view (FOV) of camera 108 is related to the possible range of head movements made by user 150, while maintaining the eyes within the image frame. System 100 may include multiple cameras 108 with different FOVs, allowing for imaging of a wider overall FOV than would be possible with a single camera 108.

Camera 108 may be any type of device capable of acquiring an image representation of a real-world scene, including the acquisition of any form of electromagnetic radiation at any range of wavelengths (e.g., light in the visible or non-visible spectrum, ultraviolet, infrared, radar, microwave, RF, and the like). For example, camera 108 may be a complementary metal-oxide-semiconductor (CMOS) or charge-coupled device (CCD) camera operating in the visible to near infrared (NIR) spectrum. In general, camera 108 is operative in a spectral region that corresponds to or at least partially overlaps with, the operational wavelength range of light source 106. The main components of camera 108 are: a filter 111, an image sensor 110, a lens (not shown), and electronic circuitry (not shown). Image sensor 110 may be configured to detect light at selected wavelengths only (i.e., a narrow-band sensor). Alternatively, filter 111 may be configured to block light outside the desired wavelengths from reaching image sensor 110 (e.g., using a band-pass filter).

Sensor 110 may be, for example, a photodiode, a CCD, or another type of light detection element. Camera 108 is generally operative to acquire at least one image frame, such as a sequence of consecutive image frames representing a video image, which may be converted into an electronic signal for subsequent processing and/or transmission. As an example, camera 108 may be embodied by a modified web camera, a digital camera and/or a cellular phone camera. Accordingly, the term "image" as used herein refers to any form of output from an aforementioned image sensor, including any optical or digital representation of a scene acquired at any spectral region, and encompasses both a single image frame and a sequence of image frames (i.e., a "video image").

It is noted that system 100 may include an alternative sensor, instead of camera 108, which is configured to determine the relative eye orientation of user 150. For example, system 100 may alternatively include at least one discrete light sensor, such as one or more infrared (IR) sensors, arranged individually or in a sensor array. Such sensors may allow for the determination of the relative position of the pupil based on an analysis of the reflected light detected by to the sensor(s), which provide an indication of the relative direction that user 150 is looking. In such an embodiment, the term image refers to the correlative signal that is produced. Primary display 102 and auxiliary display 124 are configured to display visual information that is viewable by user 150. The displayed information may include graphical control elements with selectable options, such as in the form of graphical menus or tables containing alphanumeric characters and/or symbols (as will be elaborated upon further herein-below). Primary display 102 may be any device or mechanism capable of presenting visual information using any suitable format or underlying technology, including but not limited to: a computer monitor, a television monitor, a tablet or mobile phone display, a plasma or LCD screen, a light emitting diode (LED) display, a three-dimensional representation display (e.g., a holographic display), and the like. Primary display 102 may be embodied by a head-mounted display (HMD) embedded within a wearable apparatus worn by user 150, such as a helmet, a headband, a visor, spectacles, goggles, and the like. System 100 may alternatively include an audible interface and/or a tactile interface, in addition to or instead of primary display 102 and auxiliary display 124, to provide audible and/or tactile communication adapted to the requirement of user 150.

Processor 104 receives instructions and data from the various system components. Processor 104 is also configured to perform image processing and analysis on the image frames captured by camera 108, and to extract information from the image characteristics. Processor 104 may be situated at a remote location from the other components of system 100. For example, processor 104 may be part of a server, such as a remote computer or remote computing system or machine, which is accessible over a communications medium or network. Alternatively, processor 104 may be situated adjacent to user 150 and/or integrated within other components of system 100. As an example, processor 104 may be embodied by a low cost processor with sufficient computing power (e.g., Odroid U3 or Raspberry pi2) including a text to speech engine (not shown) and Bluetooth capabilities.

Audio unit 112 is configured to generate an audible output. The audible output may include different types of sounds of varying tones or intensities, ranging from simple beeps or alarm type audio notifications to more complex speech patterns. System 100 may generally include multiple audio units 112, which may be configured to produce multiple forms of audible output. Audio unit 112 may be embodied by at least one speaker, such as a pair of headphones.

Computing device 114 may be embodied by a mobile computing device, such as a smartphone, a tablet computer, and/or a digital music player, or a stationary computing device, such as a desktop computer.

System 100 may include or be used with a support frame (not shown) for supporting elements of system 100 attached, adjacent to or nearby user 150. The support frame may be embodied by a spectacle or eye-glasses. The support frame may support light source 106 and camera 108 using a strong but flexible, moveable arm (not shown). The flexible movable arm can be made of a material that is strong and rigid enough to support camera 108 and yet flexible enough to be bent to adjust the imaging range, location and/or viewing angle of camera 108. In order to reduce weight and pressure on user 150, a light-weight material may be used. For example, camera 108 may be attached via a wire to a head gear worn by and directed toward the face of user 150, such that camera 108 images at least one eye of user 150. This alignment may be readjusted automatically or manually to maintain alignment of the eyes during shifting head movements of user 150 or to accommodate other physical requirements of user 150.

ALS patients and others patients can require ventilators or other equipment to be connected to their nostrils or other body parts, so the maneuverability of the flexible arm can help allow such patients to use system 100 easily and conveniently without some of the interference or constraints that would result from the system being fixed in place. To fit the needs of different users (e.g., users with different types of respirators), the support frame can be designed with a strong support frame that may hold selected components of system 100 in a relatively steady and stable state. Another example, is attaching system 100 to an independent surface, such as to an adjacent counter, a vehicle or a wheelchair.

The components and devices of system 100 may be based in hardware, software, or combinations thereof. It is appreciated that the functionality associated with each of the devices or components of system 100 may be distributed among multiple devices or components, which may reside at a single location or at multiple locations. For example, the functionality associated with processor 104 may be distributed between multiple processing units (such as a dedicated image processor for the image processing functions). System 100 may optionally include and/or be associated with additional components not shown in FIG. 1, for enabling the implementation of the disclosed subject matter. For example, system 100 may include a power supply (not shown) for providing power to the various components, and may further include a memory or storage unit (not shown) for temporary storage of image frames or other types of data.

The operation of system 100 will now be discussed, for exemplary purposes, in the context of a user 150 characterized by a difficulty or inability to verbally communicate (e.g., such as a patient with locked-in syndrome). User 150 views visual information presented on primary display 102, and/or auxiliary display 124, such as multiple command selections. Camera 108 captures images of the eyes of user 150 which are illuminated by light source 106. Processor 104 receives and processes the captured images. In particular, processor 104 compares a captured image of the eye of user 150 to at least one previous captured image, to determine the relative orientation of the pupil within the eye socket (or changes in the pupil orientation). Relative eye orientation represents the general direction that user 150 is looking relative to the orientation of the head (e.g., "up", "down", "left", "right", "straight ahead"). A plurality of options is presented on an option selection table or menu displayed on display 102, 124 that are selected by the relative movement of the eye of user 150.

The operation of system 100 with an alternative sensor instead of camera 108 will be further discussed, for exemplary purposes, implementing a series of IR light sensors. Each IR light sensor will be arranged to receive light reflection from the illuminated eye of user 150 at a different point around the eye of user 150 (e.g., four evenly distributed IR light sensors). Each IR light sensor will receive light and signal to processor 104, which is processed algorithmically, comparing the respective signals of the different IR light sensors. Processor 104 determines the relative eye orientation from the relative proximity of the pupil of user 150 to the IR light sensors, i.e., a relative direction user 150 is gazing.

The direction user 150 is looking, and hence the relative orientation of the pupil in the captured image, is influenced by the specific option displayed on display 102, 124 that is desired by user 150. In this way, system 100 can determine the relative eye orientation of user 150 and apply the determined relative eye orientation to the information displayed on display 102, 124 to determine a selection of an option by user 150. In this manner, processor 104 determines the user selection based only on a relative eye orientation, without determining a precise focal location of the user (i.e., without determining the particular spot or spatial coordinates that user 150 is looking at in relation to a particular frame of reference, such as display 102, 124).

Processor 104 provides instructions to display 102, audio unit 112, and/or computing device 114 to perform an action based on the determined selection of user 150. These actions can be, for example: to audibly output a word, letter, phrase, sentence or alarm warning siren, to display a different menu screen or different menu option(s), to affect a written text, to send a text message or e-mail, or to affect an application being executed on computing device 114. The verbal, textual and visual outputs of the system 100 allow user 150 to use his/her eye gaze indications to communicate with (facilitate communication with) the outside world.

Figure 2:
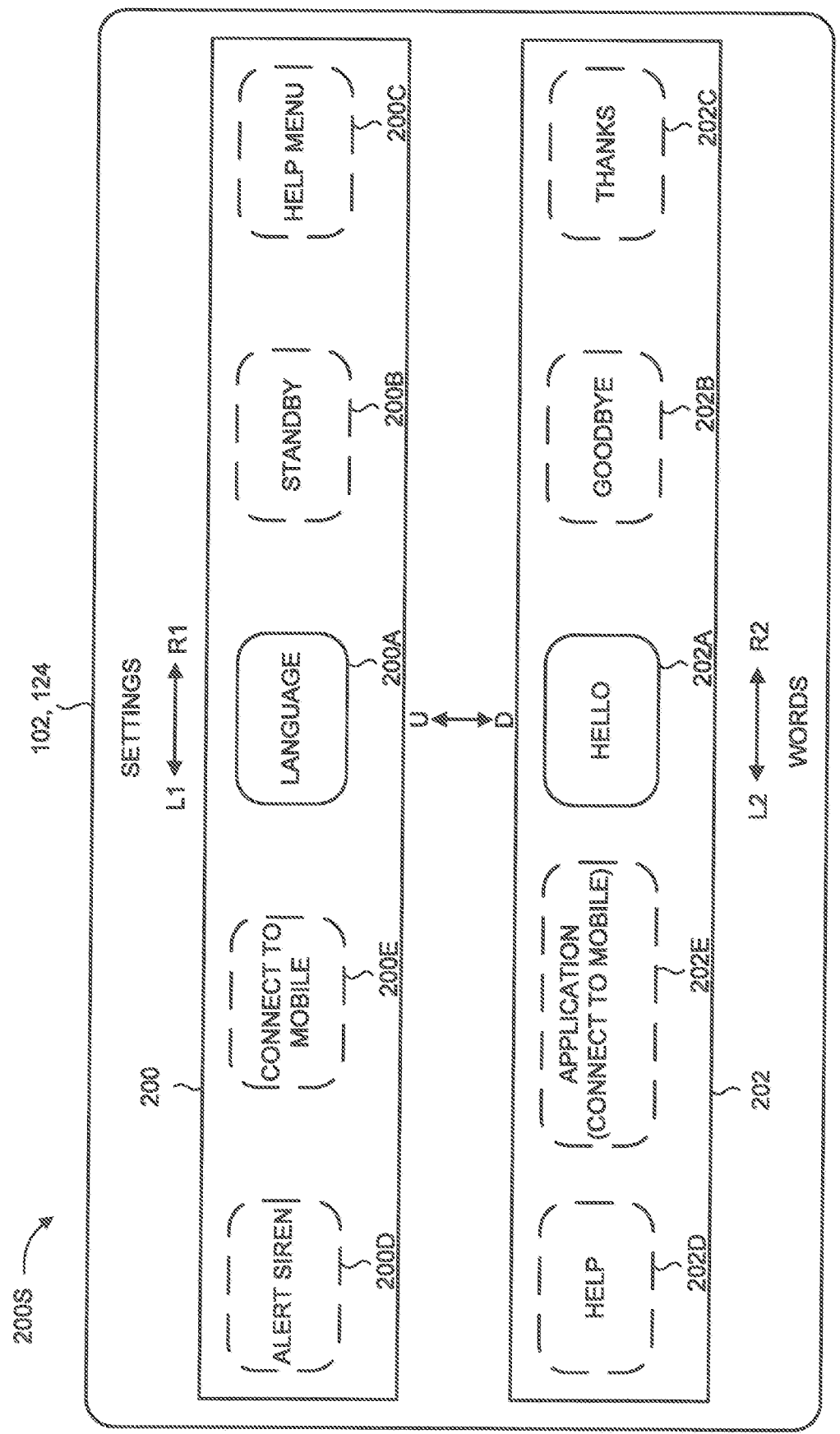
FIG. 2 is an illustration of a settings menu and a words menu displayed on the display of FIG. 1.

The selection process of system 100 will now be further described with reference to FIGS. 2 to 4. FIGS. 2 to 4 are illustrations of option selection tables or menus displayed on primary display 102 and/or auxiliary display 124 of FIG. 1. In the exemplary display screen 200S depicted in FIG. 2, two separate menu portions are shown. The upper menu portion 200 is a "settings menu", which is arranged to allow user 150 to select or alter a setting parameter of system 100. The lower menu portion 202 is a "word menu", which is arranged to allow user 150 to select a specific word or series of words (a phrase) from a predetermined set of key words and phrases. One or more setting options 200A, 200B, 200C, 200D, 200E and one or more word options 202A, 202B, 202C 202D, 202E are displayed on display 102, 124 at a time. Selection of an option can lead to a sub-menu with additional options.

In the illustrated example, option 200A represents a "language option" that leads to a sub-menu of different languages to choose from. Option 200B represents a "standby option" that switches system 100 into a standby (i.e., rest or low power) mode of operation until reactivated by user 150, such as by performing a specific eye gesture or indication. Option 200C represents a "help option" that leads to a sub-menu of different options designed to help user 150 (e.g., explanations of how to use certain aspects or elements of system 100). Option 200D represents an "alert option" that when selected causes audio unit 112 to emit a warning or alert signal. Option 200D is especially useful when user 150 is in distress and/or a life-threatening situation. The warning or alert siren may also be activated by user 150 performing a specific eye gesture or indication, such as by winking four times in rapid succession. Option 200E represents a "connect to mobile option" that establishes a communication link 116 between processor 104 and computing device 114, allowing user 150 to execute program applications on computing device 114.

Referring to the word menu portion 202, option 202A represents the word: "hello"; option 202B represents the word: "goodbye"; option 202C represents the word: "thanks"; and option 202D represents the word: "help". For example, selection of option 202D may cause audio unit 112 to emit a warning signal or alert siren, similar to settings option 200D. Option 202E represents the word: "application". For example, selection of option 202E may direct processor 104 to establish a communication link 116 with computing device 114 to allow the user to execute program applications on computing device 114, similar to setting option 200E.

In an exemplary embodiment, only a single option from either "settings" menu portion 200 or "words" menu portion 202 is displayed at a given time on display 102, 124, allowing user 150 to either select the currently displayed menu option or to continue viewing other available menu options, by implementing suitable eye movements or gestures. For example, individual options from each menu portion 200, 202 may be presented sequentially in a cyclic manner, in accordance with the relative eye orientation of user 150. In particular, user 150 may initially select "settings menu" 200 by looking in an upwards direction (U). Subsequently, by looking leftwards (L1) user 150 may cycle through the "settings options" presented on display 102, 124 in a first sequential order, whereas by looking rightwards (R1) user 150 can cycle through the "settings options" in a reverse sequential order. For example, display 102, 124 initially presents only settings options 200A and 202A. By looking up (U) and then toward the left (L1), user 150 can direct system 100 to display settings option 200E (e.g., in place of settings option 200A). Alternatively, by looking up (U) and then toward the right (R1), user 150 can direct system 100 to display option 200B (e.g., in place of option 200A). Similarly, by looking down (D) initially, user 150 can select "words menu" 202. Subsequently, user 150 may sequentially cycle through the "words options" on display, such as by looking left (L2) to cycle through the words options in a first sequential order or by looking right (R2) to cycle through the words options in a second sequential order. For example, by looking down (D) and then toward the left (L2), user 150 can direct system 100 to display word option 202E (e.g., in place of option 202A). Alternatively, by looking down (D) and then toward the right (R2), user 150 can direct system 100 to display option 202B (e.g., in place of option 202A). It is noted that alternative directional configurations are equally applicable. For example, user 150 may alternatively sequentially cycle through menu options by directing his eye gaze upwards and downwards rather than leftwards and rightwards, and display 102, 124 may present different menu portions 200, 202 side-by-side rather than in a top-and-bottom configuration. It is additionally noted that the aforementioned example is applicable only if system 100 employs a visual display option. Alternatively, system 100 may include an audible interface (such as audio unit 112) instead of a display unit, such that the actions are presented to user 150 audibly.

User 150 can use a predetermined eye-based gesture or indication, such as closing their eye (winking/blinking), or gazing in a specified direction, such as a diagonal or slanted angle relative to a forward relative eye orientation (e.g., a 45 degree angle), to select an option from one of the menus 200, 202. User 150 may select a suitable eye-based gesture to be used during an initialization process of system 100, so as to ensure that he/she can successfully implement the selection process (for example, some users may have difficulty blinking and so would select an alternative gesture instead). The selected gesture may be a preselected, default option so as to avoid the need for initial setup, allowing system 100 to be used immediately without further initialization. For example, user 150 can look down (D) and then toward the left (L2) and/or right (R2) to cycle through the different options of word menu 202 until he/she arrives at the desired option, e.g., option 202C, and then look down (D) and gesture (e.g., winking) to select option 202C (the word "thanks"). Selection of a word in the word menu 202 will direct audio unit 112 to provide an audible indication of the selected word. For example, selecting option 202C will cause those in the vicinity of user 150 to hear the word "thanks" audibly emitted from audio unit 112.

A temporary visual indication, such as, highlighted, emboldened text, or a colored frame may be applied to the selected option, for example to indicate that an option has been initially or tentatively selected, but not yet validated by user 150. A confirmation gesture or indication (such as blinking or an alternative eye-related gesture) may then be required in order to validate the user's selection of an option, before implementing the relevant functionality associated with the selected option. In addition, shapes or colors may be used to assist with the differentiation of different options in the presented menus. Alternatively, a tentative user selection may be indicated audibly, such as by directing partial audio output to user 150. For example, the menu option that is initially (tentatively) selected is broadcast only through a single channel of audio headphones being worn by user 150, providing a monophonic sound reproduction (e.g., by broadcasting only to the right ear/right channel of the headphones). When user 150 wants to make the word heard by his surrounding environment, the selected word is validated by an additional eye-related indication or gesture (e.g., blinking), which causes an appropriate sound (or sounds) associated with the selected option to be broadcast over audio unit 112, as well as optionally over the other audio channel of the headphones worn by user 150 (e.g., the left ear/left channel of the headphones). By selectively directing partial audible indications between different audio units 112 (e.g., between headphones listenable by the user only and speakers listenable by the entire surroundings), and between different audio channels of a single audio unit (i.e., mono broadcasting), user 150 can recognize and control the audible feedback that is broadcast to their surroundings by system 100.

In another embodiment of the present invention, audio unit 112 may provide an audible indication of the available selection options to user 150, such as in addition to or instead of the visual presentation viewable on primary display 102 (i.e., by supplementing and/or replacing primary display 102 and/or auxiliary display 124 entirely). For example, the list of settings options of settings menu 200 and/or word options of words menu 202 may be broadcast to user 150 through headphones, so user 150 will be able to hear the available options and/or along with the different eye-related gestures associated with each available option. For example, the user 150 may hear the following audio sequence to prompt a user selection: "left—hello, right—goodbye, up—yes, down—no, blink—repeat menu". Alternatively, user 150 may simply hear a single option, e.g., "language". The option(s) may be broadcast only to user 150. User 150 may then move on to a different option or select an option by an implementation of the appropriate eye-related gesture, following which the associated audio output (e.g., speaking the selected word) may be publically broadcast to the surroundings. As such, the selection interface of system 100 can be a visual interface (a visual menu presented on display 102, 124) and/or an audible interface (an audible menu provided by processor 104 and audio unit 112).

In the operation without a display, user 150 may hear words in broadcast over his/her headphone, and cycles between different word options using glances to either side (e.g., right or left, up or down) and gestures (e.g., blinks or winks) in order to make a selection. Even without a display, system 100 can present audible menus that are similar to the visual menus, e.g., settings menu 200 and words menu 202, described hereinabove. It will be appreciated that the elimination of a display may be particularly beneficial in medical institutions, where the system of the present invention can allow a recovering patient, e.g., after a surgery, to request a nurse or to communicate with family members, similar to a distress device that can be placed next to a patient's bed. Furthermore, excluding a primary display decreases the number of components of the system, which as a result can lower the overall cost and make the system more mobile and accessible. It is noted that when operating without a primary display, the system of the present invention still uses eye gestures to help user 150 communicate via audio output from audio unit 112, and may further use computing device 114, such as in order to write new words and send them to processor 104.

Referring to the exemplary display screen 200S of FIG. 2, display 102, 124 may alternatively selectively display only a single menu portion 200, 202 at a given instant, while presenting a selectable option on each of the menus 200, 202 that would allow for displaying the other menu 200, 202 instead (or an alternative available menu that is not currently being displayed). For example, settings menu 200 may include a "switch to words menu" option (not shown), and correspondingly words menu 202 may include a "switch to settings menu" option (not shown), allowing for toggling between the two respective menus 200, 202. Such a display configuration may serve to simplify the selection process by limiting the eye movements of user 150 to only the left or right directions (and obviating the need for upward and downward eye movements). It will be further appreciated that the ability to sequentially cycle through the displayed menus 200, 202 by merely shifting his/her gaze toward a general direction (e.g., left or right) allows user 150 to access all of the available menu options relatively easily and quickly. For example, if a particular menu consists of ten (10) possible options, any one of the options can be reached within five (5) "cycles" of the menu (e.g., in the example of FIG. 2 where words menu 202 includes five options, then option 202D can be reached starting from option 202A by cycling either twice to the left or three times to the right). The vocabulary provided in words menu 202 can be limited to a certain number of pre-determined words that were found to have high importance and high incidence to the target audience or user in question. The available word options of a given words menu 202 may also be preselected and/or edited by user 150, partially or entirely. The respective audio outputs associated with the words menu 202 vocabulary may be previously generated prior to the operation of system 100 (e.g., by pre-recording various audio files corresponding to spoken words and/or phrases), or may be generated in real-time (e.g., via text-to-speech or phonetic transcription speech synthesizers).

As mentioned above, a given menu option may represent a different sub-menu that can be displayed, such as, words menu 202, including a menu option representing a letter group menu. Alternatively, selection of a connect to mobile option 200E, 202E on words menu 202 can cause processor 104 to form a communication link 116 with computing device 114 which is executing an application that includes a different menu or sub-menu, e.g., a letter group menu.

Figure 3A:
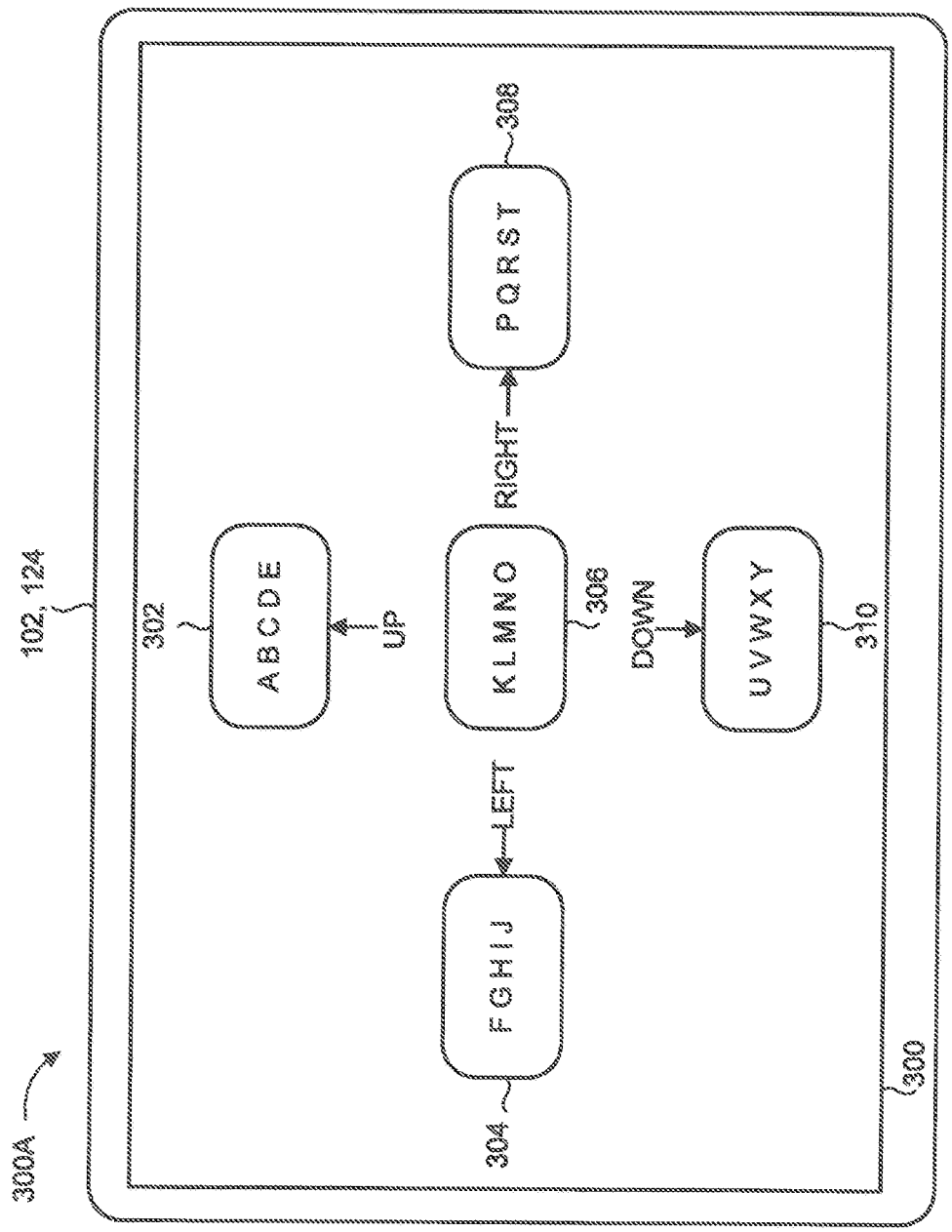
FIG. 3A is an illustration of a letter group menu displayed on the display of FIG. 1.

Reference is now made to FIG. 3A, which is an illustration of the exemplary display screen 300A on display 102, 124 presenting an exemplary letter option menu, generally referenced 300, that includes different letter group options 302, 304, 306, 308, 310 for selection. Letter group menu 300 may be used for composing a written text or message, or for spelling out a word to be communicated or added to words menu 202. In the illustrated example of FIG. 3A, option 302 represents the group of letters: "ABCDE"; option 304 represents the letters: "FGHIJ"; option 306 represents the letters: "KLMNO"; option 308 represents the letters: "PQRST"; and option 310 represents the letters: "UVWXY". Letter group options 302, 304, 306, 308, 310 are presented in a cross configuration, with each letter group located on a separate region of display 102, 124 (i.e., top, bottom, left, right, or middle). Analogous to the selection of menu options previously described with reference to FIG. 2, user 150 may select an available option of letter group menu 300 using only relative eye orientation and/or eye-related gestures. For example, while viewing letter group menu 300 on display 102, 124, user 150 may gaze upward (U) to select option 302; may gaze leftwards (L) to select option 304; may gaze rightwards (R) to select option 308; or may gaze downwards (D) to select option 310. User 150 may select the middle option 306 by performing a predetermined eye-related gesture or indication, such as closing one or both eyes (winking/blinking), or gazing in a diagonal or slanted angle relative to a forward relative eye orientation (e.g., a 45 degree angle). The options could also be communicated via audio unit 112 announcing the aforementioned letters.

A selection of a letter group option (e.g., 302 or 304) of letter group menu 300 may then result in displaying another sub-menu representing the individual letters of the selected letter group (i.e., 400). For example, if user 150 gazes up to select letter group option 302 (letters ABCDE), display 102, 124 then displays the associated ABCDE letter sub-menu. Reference is now made to FIG. 4, which is an illustration of the exemplary display screen 400A on display 102, 124 presenting the ABCDE letter sub-menu, generally referenced 400, that includes different individual letter options 402, 404, 406, 408, 410 for selection. Letter sub-menu 400 corresponds to the selected letter group option 302 (FIG. 3A). In the illustrated example of menu 400, option 402 represents the letter "A"; option 404 represents the letter "B"; option 406 represents the letter "C"; option 408 represents the letter "D"; and option 410 represents the letter "E". Similar to letter group menu 300, individual letter options are also presented in a cross configuration, with each letter group located on a separate region of display 102, 124 (i.e., top, bottom, left, right, or middle). User 150 may select an available option of individual letter sub-menu 400 using relative eye orientation and/or eye-related gestures. For example, user 150 may gaze upwards (U) to select option 402; may gaze leftwards (L) to select option 404; may gaze rightwards (R) to select option 408; and may gaze downwards (D) to select option 410. User 150 may select the middle option 406 by performing a predetermined eye-related gesture or indication, such as closing one or both eyes (winking/blinking).

A selection of an individual letter of sub-menu 400 may then result in a visual indication of the selected letter displayed on primary display 102 and/or auxiliary display 124 (e.g., by highlighting or presenting a visual border around the selected letter, which may require confirmation by user 150. Alternatively or additionally, an audio indication of the selected letter may be generated by audio unit 112. The selected letter may further be added to a text message or text-based instruction being composed by user 150. For example, looking up and selecting option 402 directs audio unit 112 to emit the sound of the letter "A", while providing a visual indication of the displayed letter "A" on primary display 102 (and/or auxiliary display 124), and entering the letter "A" into the text of a message being composed by user 150. A completed word may be added and saved to words menu 202.

It is noted that letter group menu 300 or individual letter menu 400 may be alternatively configured to display any number of options (and not necessarily five options). For example, if user 150 experiences difficulties in implementing a suitable eye gesture to indicate the selection of the "middle" option, only four options may be displayed. In this manner, the visually presented menu can be configured to obtain the user selection based solely on a more standard selection of relative eye orientation of the user (e.g., up, down, left or right), while precluding the need for any additional eye-related gestures. The middle region of a menu that includes only 4 options may be left empty, or may display the title of the menu (i.e., not an option that can be selected). Alternatively, system 100 can use four diagonal directions (up-right, up-left, down-right, down-left) and optionally at least direct direction (e.g., straight down) for selection, such as for those that have difficulty controlling their blinking or experience involuntary blinking.

The different menu options may also be displayed with unique visual effects or characteristics, so as to provide additional visual differentiation to each displayed menu option, in addition to their different relative locations on display 102, 124. For example, each menu option can be displayed in a different color shape or style of border, so that the different options can be more easily recognized, identified and distinguished from one another by user 150. A menu may include a "return option" to enable user 150 to go back to a previous selected option, to a previously displayed menu or a preset determined action. Alternatively, system 100 may be configured such that user 150 can be automatically returned to a prior menu or a default menu following the final selection of a menu option. As mentioned above, an indication may be provided to the selected option to indicate that the option has been initially selected. The indication may be, for example, a highlighted or emboldened text, a colored frame, and/or an audible indication emitted in at least one ear of the headphones worn by user 150. System 100 may then wait for a confirmation gesture or indication (such as blink or certain eye movement) to validate or confirm the selection of the selected option, thereby providing a visual and/or audio indication informing user 150 that an option has been selected and/or which option has been selected.

An eye-related gesture for implementing a selection of an option by user 150 can include a sequence of individual actions or gestures. Such a sequence may also allow for the direct selection of an available option in a sub-menu associated with the presented menu while bypassing the presentation of the sub-menu. For example, user 150 can select an individual letter by performing two consecutive predetermined eye-related gestures while viewing "letter group menu" 300 of FIG. 3A, without being displayed the "individual letter sub-menu" 400 of FIG. 4. The first gesture would select a particular letter group (e.g., letter group 308), and then the second gesture, which may be based on the color or location of an individual letter within the letter group, selects a specific letter (e.g., the letter "S"), thereby bypassing the displaying of individual letter sub-menu 400. For example, the individual letters inside each displayed letter-group 302, 304, 306, 308, 310 may be color coded to correspond with a respective direction, which may be indicated by a color indicator displayed in the relevant direction. For example, the first letters of each letter-group: "A", "F", "K", "P", and "U", may all be depicted in one color (e.g., orange), and an orange color indicator may be displayed on display 102, 124 represented by an arrow facing a certain direction (e.g., up). Accordingly, by first looking left (L), user 150 selects option 304 (i.e., the entire letter group: "FGHIJ"), and by subsequently looking upward (UP) (i.e., towards the orange indicator direction), user 150 selects a specific letter (e.g., the letter "F") from among letter group 304. The colors used to display selected menu options can be specific colors that are easily discernible and highly conspicuous, to ensure their perception even by users 150 characterized by impaired vision or perception capabilities. It is noted that the graphical elements of menu items displayed by display 102, 124 is not limited to text or alphanumeric characters, but can also include, for example, various types of symbols, icons or images representing various actions or selectable options, such as: a "spacebar icon", a "backspace/delete icon", a "back or return to the main menu icon", and the like. For a visual output, user 150 can be provided with an option menu with a plurality of images, symbols or pictorial drawings, e.g., a plate of food, a glass of water, a car, a wheelchair, and the like. The selected drawing can be displayed to the user's surroundings on an external screen, such as auxiliary display 124, or sent in a message to another device (e.g., to a mobile phone of a friend or a nurse). Alternatively, selection of a drawing can result in an appropriate audio output, e.g., selection of the drawing of a plate of food would result in the audible output of the word "food".

System 100 can include word prediction applications to help forecast and suggest complete words based on the first few letters selected by a user. For example, if user 150 selects the following letter sequence: "H-E-L", system 100 can suggest the words: "help" or "hello", by presenting the suggested words on display 102, 124 or via audio unit 112.

System 100 may even utilize entire word or sentence completion based on context determined by processor 104. User 150 can cycle through different suggested complete words on display, such as by looking towards the left or right. Selection of a suggested word by user 150 can be performed with a suitable eye-related gesture or indication. In this manner, the selection of a word by user 150 may be hastened and the accuracy improved (by precluding the need for user 150 to continue selecting the additional letter and avoiding subsequent inadvertent incorrect letter selections by the user). The completed words can be indicated audibly or visually, and stored or transferred as an audio file and/or text file, as applicable. The word prediction feature may be based on language modeling and vocabulary libraries, and may be adaptive such as by learning the language habits of a user to improve future suggested word completions associated with that user.

Rather than indicating a word by spelling out the individual letters, user 150 may locate the desired word directly on a displayed "word menu". Such a menu can include different options representing actual words or categories of words classified by topic or subject matter, (e.g., "food", "clothing", "colors", and the like). The selection of an initially displayed word option can result in the displaying of a sub-menu with logical word options that follow from the initially selected word. For example, a word menu may initially present five different categories. When a particular category is selected, a sub-menu of five new words within that category is then presented. Each of these new words may lead to further subcategories, and so forth (e.g., "clothing"-"shirt"-"dress shirt"). In this manner, a substantially large vocabulary of potential words is made available to user 150. For example, assuming each word menu screen presents a total of 5 options, user 150 can potentially access over three thousand (3000) different words using only five (5) eye-related gestures (i.e., when each option on the first four menu screens represents a sub-category of word options).

User 150 can save preferred frequent words or sentences, allowing direct access to such words/sentences in future operational sessions. System 100 can also adaptively learn preferences and habits of user 150, and amend or update the available words or options of different menu screens accordingly. By prioritizing preferred or frequent words or options previously selected by the user, the operation of system 100 may become more efficient and more intuitive. System 100 may further include an interface (not shown), such as via the internet, an input device coupled with processor, or an application of computing device 114, to allow a particular user (or an administrator), to customize a particular menu for that user. Such menu customization allow for individual users or a particular group of users to select from words that are more relevant or more likely to be frequently accessed by such users/groups. This customization also serves to accommodate a range of different users with special needs of various types.

Figure 3B:
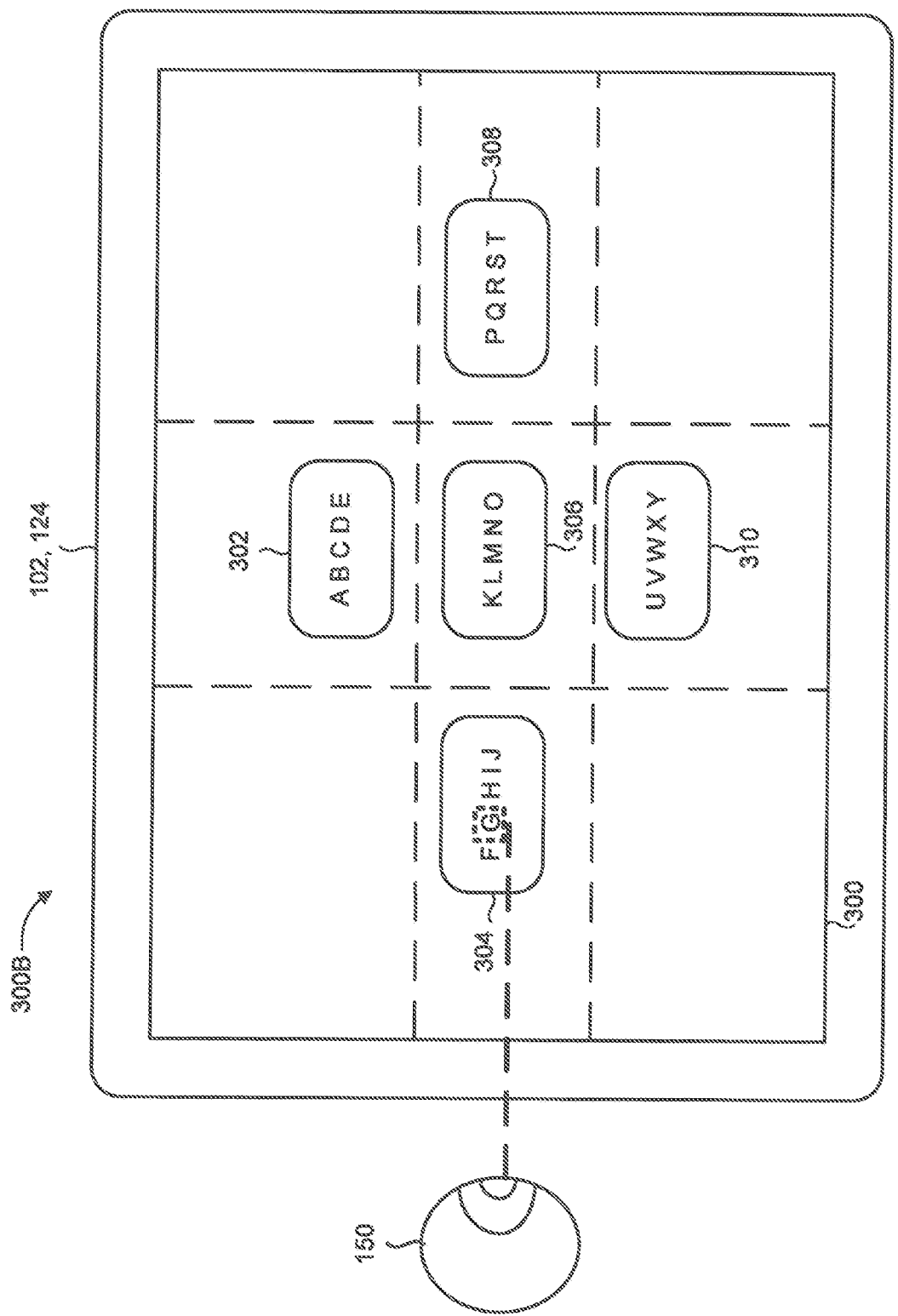
FIG. 3B is an illustration of the letter group menu of FIG. 3A where the image to be displayed on the display has been divided into different sections, and a selection is being made.

FIG. 3B is an illustration of the exemplary display screen 300B on display 102, 124 presenting the exemplary letter group menu 300 of FIG. 3A divided into different sections. In FIG. 3B a selection of the letter "G" is being made.

Reference is now made to FIGS. 5A to 5F. FIGS. 5A to 5F are schematic illustrations of exemplary images of an eye of user 150 captured by camera 108 of system 100 of FIG. 1. Each image (500A, 500B, 500C, 500D, 500E, 500F) is divided into four quadrants: upper quadrant 502 which corresponds to user 150 looking up; lower quadrant 504 which corresponds to user 150 looking down; left quadrant 506 which corresponds to user 150 looking right; and right quadrant 508 which corresponds to user 150 looking left. Processor 104 determines the coarse or general location of the eye pupil in the captured image. For example, processor 104 may determine in which region or quadrant the pupil is most likely located (i.e., in which the majority of the pupil is located), or if the pupil is in or near the center of the image. If no pupil is located, then processor 104 may determine that the eye is blinking or winking.

Based on the general location of the pupil and/or the change in direction of the pupil (e.g., movement towards the left, right, up or down) the processor 104 determines the corresponding location on display 102, 124 (up, down, left, right, or center) and hence the selected/desired option of a menu (200, 300, 400) being displayed. For example, in image 500A (FIG. 5A), the pupil P is located in upper quadrant 502, which corresponds to option 402 of individual letters menu 400 (FIG. 4). In respective images 500B, 500C, 500D (FIGS. 5B, 5C, 5D), the pupil P is located, respectively, in lower quadrant 504, left quadrant 506, and right quadrant 508, corresponding to respective letter options 410 "E", 404 "B", and 408 "B" of individual letters menu 400 (pupil P being located in left quadrant 506 corresponds to the user looking toward the right, and pupil P being located in right quadrant 508 corresponds to the user looking toward the left [i.e., the captured image mirrors the user's gesture]). If processor 104 fails to detect (at least a minimal portion of) pupil P in an image, or throughout a minimal sequence of successive images, as shown in image 500E (FIG. 5E), then processor 104 may determine that user 150 is winking (or blinking), which may correspond to a selection of the centrally displayed option on the menu screen (e.g., option 406 of menu 400) or the selection or confirmation of an option (e.g., the letter 410 "E"). If processor 104 detects pupil P to be in or near the center of an image, or throughout a minimal sequence of successive images, as shown in image 500F (FIG. 5F), then processor 104 may determine that user 150 is looking forward (not toward any of the above-mentioned directions), which may correspond to a standby mode where system 100 waits until user 150 looks in a direction or performs an eye gesture. The actual number of divisions may vary and is not limited to quadrants.

It will be appreciated that it is sufficient for processor 104 to determine only the relative eye orientation with regards to the head or eye socket of the user 150 (i.e., up, down, left, right, or center). Determining the relative eye orientation generally involves relatively basic and rapid processing, rather than attempting to identify an exact gaze point location of user 150 (i.e., by determining precise location coordinates on display 102, 124 corresponding to the user line-of-sight) which involves more extensive and time-consuming processing. Accordingly, system 100 can be considered to operate in a manner resembling that of a joystick (where a direction decision is used) to provide an indication of the user selection, rather than an input similar to a mouse cursor (where pinpoint location is necessary). This "joystick" approach provides the ability to communicate by tracking the movement and/or orientation of the pupil, maintaining simplicity and convenience by simulating a joystick instead of a screen-dependent, pinpoint mouse type tracking system. Such an eye-joystick can control a selection interface (including a table or menu presented audibly and/or visually to the user) and provide audio and/or visual output.

Alternatively, instead of dividing the image 500 into quadrants, the image can be divided into additional or fewer sections during the image processing for identifying the pupil location (and relative eye orientation). For example, processor 104 may divide a captured eye image into only two sections (e.g., a left section and a right section, divided by a central vertical divider), to determine only left and right locations of the pupil. Alternatively, processor 104 may divide a captured eye image into upper and lower section (i.e., via a central horizontal boundary), to determine only up and down locations of the pupil. Further alternatively, the eye image can be divided into eight (8) sections (resembling a hashtag or number sign), to requiring more accurate determination of the angular positioning and/or movement of the pupil and corresponding relative eye orientation. Dividing the image into a large number of sections when processing to identify the pupil location may improve the determination of pupil location/relative eye orientation at various diagonal or slanted angles relative to a forward gaze of the user (e.g., at a 45 degree angle relative to a forward gaze direction of user 150).

More generally, processor 104 may divide an eye image into different sections, portions, or segments correlating to the particular sections or portions of display 102, 124 on which particular menu options are being presented. For example, letter group menu 300 and individual letter menu 400 present the respective menu options in a "cross" shaped configuration, and so processor 104 may divide each processed image in a similar cross-shaped manner, so as to facilitate determination of the pupil location representing which menu option is being viewed by user 150. Processor 104 may also track or locate other relevant eye parameters (e.g., the cornea), in addition to or instead of the eye pupil P, for determining the relative eye orientation of user 150.

Processor 104 may also track the location of the pupil P over a sequence of captured images. For example, processor 108 may utilize a reference image (500REF), and then compare a subsequent image (or a sequence of subsequent images) with the reference image 500REF to determine if the pupil P location has shifted relative to its location in the reference image 500REF, as well as the measured amount of movement. Such processing may be based on a calculated image filter to detect and measure differences from the original reference image and the subsequent images. It is further noted that determining only the relative eye-orientation direction of user 150, as well as tracking the eye pupil location over a sequence of captured images, serves to reduce the need to stabilize or compensate for movements of camera 108 (e.g., camera motions relative to the user eye between images) or compensating for changes in background. Thus, a calibration process may not be required.

While calibration of system 100 is not required, there are several methods of calibration that may be possible: generic factory, automatic, and manual calibration.

An exemplary, general calibration process is as follows. The first step is comparing consecutive images to detect relative changes by performing screen motion detection on the geographic area of the eye (including the pupil region). According to heuristics derived from the shape of the image, it can be assumed that the areas that change in the image represent areas of interest. The second step is marking the pupil circle as a point in space in the captured images, to follow the area of interest that signifies the location of the pupil P. The third step is setting a reference point as the center of a two-dimensional (x-y) axis grid and translating the eye movements to (x,y) coordinates on the grid. Once the calibration process determines, with a high enough probability, that pupil P is in the middle (i.e., close to the center [0,0] of the grid), a reference point is selected according to which the reference point coordinate system (grid) is built. The (x,y) coordinates represent the movement of the eye pupil P in each of the four directions (up, down, left and right). The fourth step may determine the range of motion of the user. The calibration process may adaptively learn the particular range of motion associated with different users. Different users are characterized by different physical features, including different eye and facial features.

Furthermore, the position and orientation of the camera 108 relative to the face and eye of each user will likely vary during different operational sessions of system 100. As a result, the calibration process of system 100 may adaptively learn the range of movement of pupil P on the x-y axis (grid) for each user, and adjust the range set threshold (beyond which is sent a signal for a certain direction of movement of the pupil), as necessary. Non-detection of pupil P for a minimum duration (e.g., a few milliseconds) is considered to represent a wink or blink by the user. The amount of time can be adjusted so as to prevent inadvertent identification of a selection, such as one based on the natural blinking of a user. It is further noted that the automatic calibration process (without prompting the user) of system 100 obviates the need for external (third party) assistance for each calibration. Further, the system (algorithm) identifies the pupil P and understands the relative eye orientation. Pupil detection capability includes identifying and comparing the location and range of motion and reliable detection of the presence/non-presence of the pupil P in an image 500. To do this, multiple object detection algorithms and their combinations may be used to deal with clarity issues and relatively heavy computation requirements. A dedicated calibration algorithm allows the system to calibrate itself automatically. Alternatively, a non-automatic calibration algorithm can be used that does not use any object recognition tools (feature detection). That is, the algorithm does not identify the exact location of the eye (pupil P), but compares images captured during system operation to those captured during a manual calibration.

System 100 may operate a generic factory calibration, performing a single initialization process prior to the operational session of system 100. The calibration (or initialization) may be implemented automatically using different filters or predetermined photographs designed for each of the potential relative eye orientations (e.g., up, down, left, right and center) that need to be identified during regular usage throughout an operational session. Processor 104 may apply the filters to the images 500, and determines the likelihood that a current processed image 500 is comparable to reference images 500REF. Reference images 500REF corresponding to each base situation or state. The system may grade the captured images based on the reference images 500REF and choose the option with the highest grade.

System 100 may also operate with self-calibration or "automatic calibration", i.e., that does not require prompting the user to initiate, but rather is performed automatically during the course of an operational session without the conscious knowledge of the user. System 100 may determine when and how often to perform a calibration process automatically, in accordance with relevant criteria. Automatic calibration can be performed when a predetermined condition is met, such as when the system is able to identify the pupil in an image.

System 100 may also operate with user or manual calibration with user 150 by providing an audio or a visual instruction, e.g., "Please Look Right", before capturing a reference image 500REF. An audio indication, such as resembling the click of a camera shutter, may be provided after the image has been captured, to notify user 150 that the image has been captured. The reference image 500REF similarly may be analyzed to locate the pupil and determine relative borders of the eye of user 150 or a determined boundary area that the pupil will approach when moving from one position to another (i.e., from "looking left" to "looking right"). This boundary area can further be used to trigger relative eye-orientation responses by user 150 as the pupil is observed or measured to cross the boundaries, resulting in processor 104 providing an appropriate response accordingly.

The captured image (signal) can be fed to a noise filter (e.g., a Markov Signal Noise filter), to reduce noise and enhance the quality of the image processing. The output for each image 500 is determined as: right, left, up, down, closed eye, center, or no identification. The final output (in this case one of five different options) can be based on additional criteria, such as, timing rules. For example, if no pupil is identified for longer than a threshold duration, such as more than approximately 0.2 seconds, then the determination is 'blink' or closed eye, and this determination could be maintained until a following image frame in which the pupil is again located or identified (i.e., movement of the pupil is detected) or to be registered as a unique action as previously mentioned.

Figure 6:
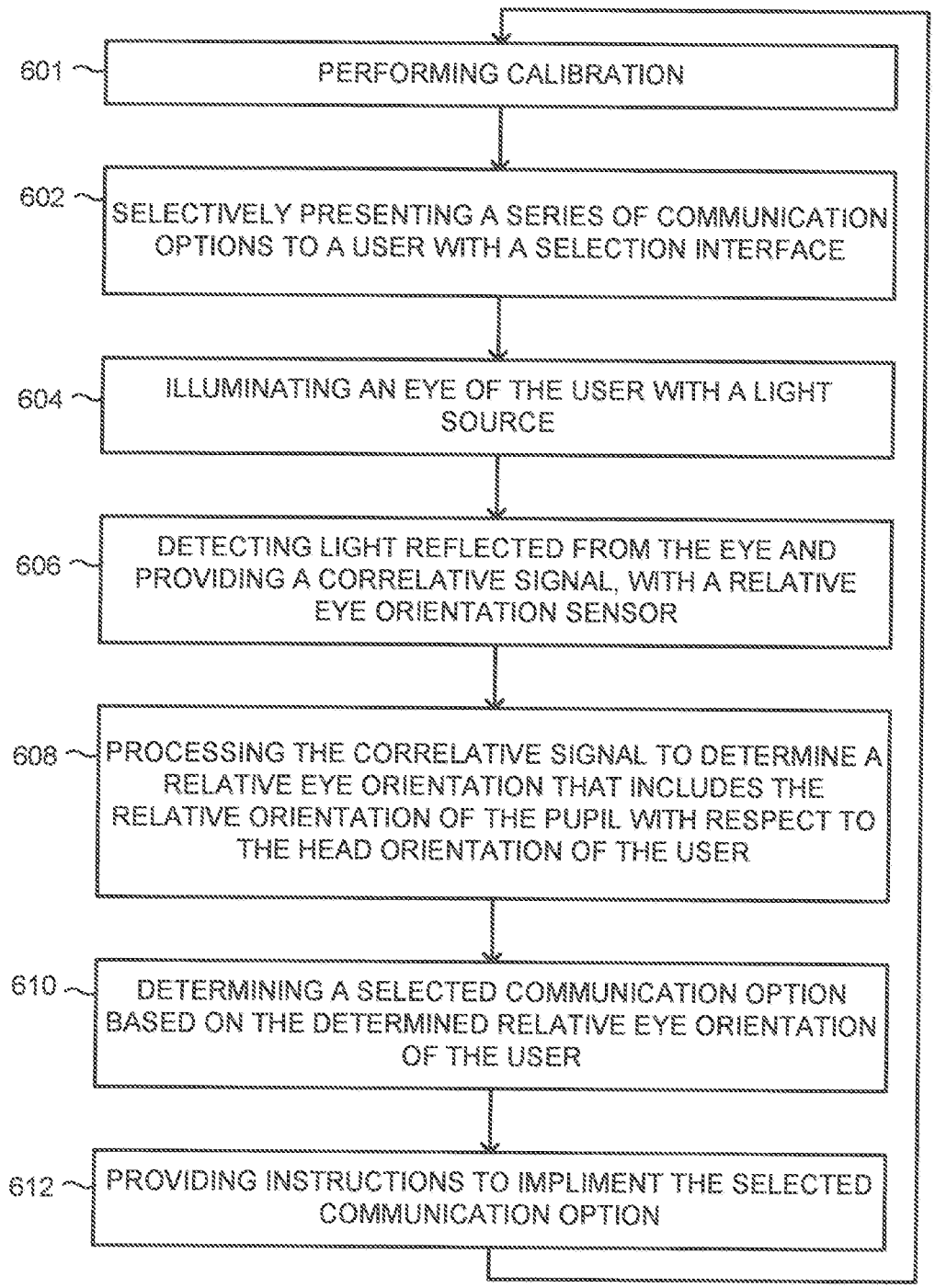
FIG. 6 is a flow diagram of a method for enabling a user to communicate with eye-based feedback operative in accordance with an embodiment of the present invention.

Reference is now made to FIG. 6, which is a flow diagram of a method for enabling a user to communicate with eye-based feedback. In an optional procedure 601, calibration is performed. Calibration of the system components may be performed only once (e.g., before the initial operation of system 100), or may be performed at regular intervals (during the operation of system 100), as necessary. Calibration may be performed using only a single eye-reflection image captured by camera 108, or by comparing and analyzing a large number of such images. Furthermore, the calibration may be adapted uniquely for specific users (i.e., for the particular user currently using system 100), or alternatively a generic calibration applicable for a large number of different users may be implemented (e.g., during an early initialization stage of system 100).

In procedure 602, a series of communication options is selectively presented to a user with a selection interface. Referring to FIGS. 1 and 3, display 102 (and/or display 124) displays a menu 300 with a variety of visual menu options 302, 304, 306, 308 and 310 for the user to choose from. The communications options may alternatively be presented via an audio or a tactile interface.

In optional procedure 604, at least one eye of the user is illuminated with a light source. Referring to FIG. 1, light source 106 emits IR light 118 toward the eyes of user 150.

Figure 5A:
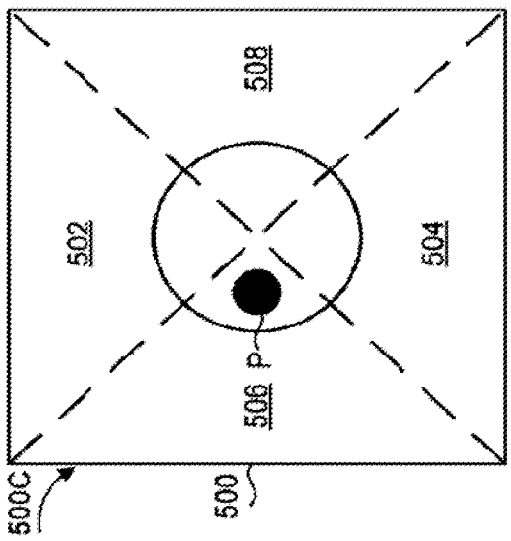
FIG. 5A is an illustration of an image of the user's eye with the pupil in an upward quadrant captured by the camera of FIG. 1.
Figure 5D:
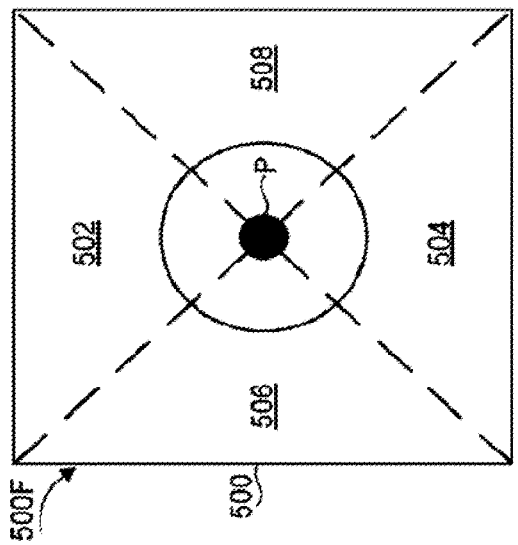
FIG. 5D is an illustration of an image of the user's eye with the pupil in a right quadrant captured by the camera of FIG. 1.
Figure 5B:
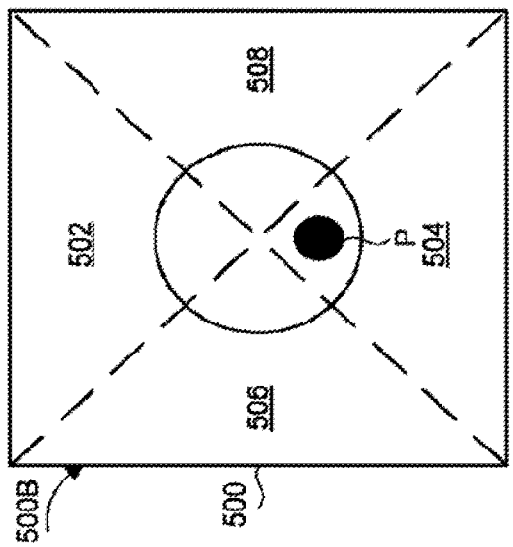
FIG. 5B is an illustration of an image of the user's eye with the pupil in a downward quadrant captured by the camera of FIG. 1.
Figure 5E:
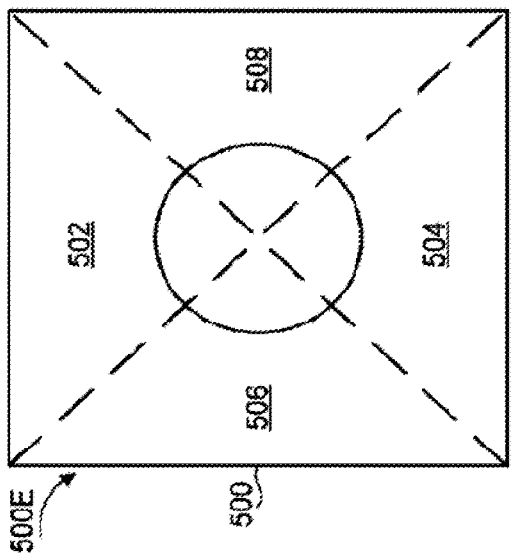
FIG. 5E is an illustration of an image of the user's eye without the pupil captured by the camera of FIG. 1.
Figure 5C:
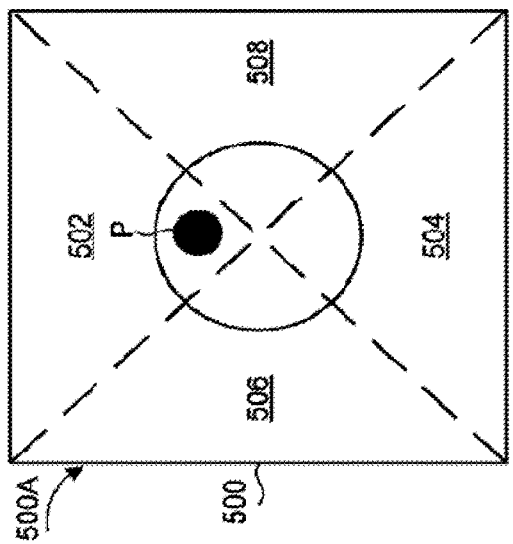
FIG. 5C is an illustration of an image of the user's eye with the pupil in a left quadrant captured by the camera of FIG. 1.
Figure 5F:
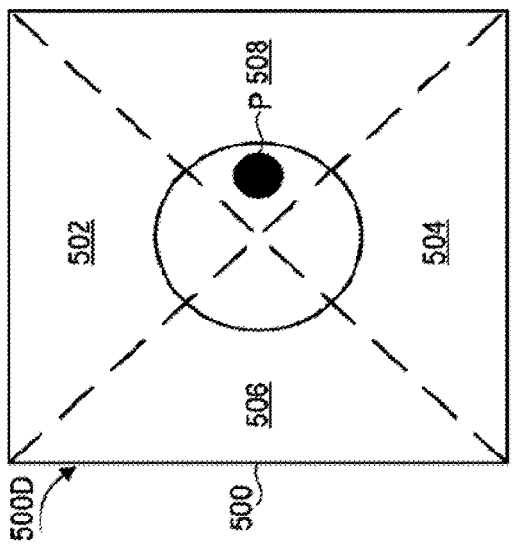
FIG. 5F is an illustration of an image of the user's eye with the pupil in the center captured by the camera of FIG. 1.

In procedure 606, light reflected from the eye is detected and a correlative signal is provided by a relative eye orientation sensor. Referring to FIG. 1, image sensor 110 receives IR light 118 reflects from the eye of user 150 and relays a correlative signal to processor 104. The eye orientation sensor may alternatively be embodied by a non-image sensor, such as by one or more discrete sensors or a sensor array. Referring to FIG. 5A, image sensor 110 generates image 500A of the region around the eye of user 150, where pupil P is located in an upper quadrant region of image 500A.

In procedure 608, the correlative signal is processed to determine a relative eye orientation that includes the relative orientation of the pupil with respect to the head orientation of the user. Referring to FIGS. 1 and 5A, processor 104 determines a relative eye orientation of user 150 based on the images captured by image sensor 110 (or by using other eye reflection data captured by a non-image sensor). The determined relative eye orientation represents the relative orientation of the pupil with respect to the head orientation of user 150 (where the head orientation represents the general direction that user 150 is facing). For example, referring to FIG. 5A, processor 104 determines from image 500A that pupil P is located in an upper quadrant region 502, and therefore the relative eye orientation of user 150 is an "up" position. Processor 104 may determine the relative eye orientation of user 150 by detecting an instantaneous relative orientation of pupil P, or by detecting a transient change of pupil P.

In procedure 610, a selected communication option is determined based on the determined relative eye orientation of the user. Referring to FIGS. 1, 5A and 3A, processor 104 selects an option presented on display 102 (and/or by audio unit 112), in accordance with the determined relative eye orientation of user 150. For example, if processor 104 determined from image 500A that the relative eye orientation of user 150 is an "up" position, processor 104 then selects communication option 302 ("ABCDE") presented on menu 300.

In procedure 612, instructions to implement the selected communication option are provided. Referring to FIG. 1, processor 104 instructs audio unit 112 to provide an audible indication associated with the selected communication option. For example, audio unit 112 broadcasts a word selected by user 150, such as the word "hello" associated with word option 202A of words menu 202. Additionally, processor 104 may instruct display 102 to present a visual indication associated with the selected communication option. For example, display 102 highlights the selected menu option, such as the "hello" word option 202A. Alternatively, processor 104 may instruct computing device 114 to implement a selected application or perform an action associated with the selected communication option. For example, computing device 114 sends a message or e-mail, such as following the selection of the "email application" option 202E of words menu 202.

As mentioned above, the processor 104 may translate the eye movements and broadcast operations through a wireless link (e.g., Bluetooth) to a computing device 114 (e.g., a smartphone) present in the area, and able to operate different applications which may be used by user 150 to communicate with his/her environment. Computing device 114 can be used to send text messages, execute different applications and/or control a computer (using programs designed for control using selection tables or menus). After the user chooses to operate an application on computing device 114, processor 104 may continue to transmit and receive data to/from computing device 114 over communication link 116.

In accordance with an embodiment of the present invention, system 100 can be used to exert control on an external device or apparatus, such as, a motorized wheelchair or computerized home appliances. For example, a user may direct or navigate a motorized wheelchair by indicating a selected direction (e.g., forward, back, left, right) using his/her relative eye orientation (e.g., up, down, left, right). The user may provide the indication by looking toward a particular menu option of a "motorized wheelchair navigation" menu presented on display 102, 124. System 100 determines the indicated selection (e.g., turn wheelchair left), and triggers the motorized wheelchair to perform the selected option. System 100 may be communicatively coupled with such external devices via a wireless communication link (e.g., communication link 116).

It is further noted that user 150 may alternatively by an individual who is vision impaired or who lacks full eye-sight capabilities, as system 100 provides eye-based communication by determining only the relative eye orientation of user 150, which does not require the full use of vision or even a satisfactory level of eye-sight to be attributed to user 150.

The present invention thus provides a relatively affordable and accessible solution with easy and intuitive operation that helps improve the quality of life of individuals with special needs, by providing means for effective communication with their environment. The system is mobile, portable and suitable for use in many situations and positions: lying, sitting, head hanging down, and the like. Furthermore, the system of the present invention does not require third party assistance for calibration.

It will be appreciated that the system and method of the present invention are not limited to individuals characterized by "locked-in syndrome", but is equally applicable for use by other types of people as well (including those who are vision impaired). The system and method of the present invention may be integrated as an application on a computing device, such as a smartphone or tablet computer or a digital music player, which includes at least a sensor for detecting light reflections from the eye (such as an embedded camera for capturing images of the eye region of the user). The system thereby facilitates or initiates different types of communication actions through the computing device based on the relative eye orientation of the user, such as by allowing the user to compose and send a message or perform a phone call.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. An eye-based communication system for enabling a user to communicate comprising:
   at least one camera for capturing images of an eye and eye socket of the user, the camera is attachable to a head gear worn by the user such that it is directed toward the face of the user; and
   a processor, communicatively coupled with said at least one camera, said processor is configured to:
      cause a speaker to audibly provide a first set of communication options to the user, each of the first set of communication options identifying a specific eye gesture for selecting a respective communication option;
      divide the image into at least two sections;
      receive and process data representative of said images to determine a location of an eye pupil of the user in one of at least two sections of said eye images;
      determine a specific eye gesture of the user based on said location;
      and
      provide at least one instruction to execute according to a first communication option from a first set of communication options based on the determined specific eye gesture as corresponding to the first communication option.

2. The system of claim 1, further comprising at least one light source, optionally comprising a light emitting diode (LED), configured to illuminate the eye of the user.

3. The system of claim 2, wherein said light source comprises an infrared (IR) light source, and wherein said at least one camera is configured to detect IR light reflected from the eye.

4. The system of claim 2, wherein at least one of said light source and said at least one camera, are coupled with a wearable head gear worn by the user or wherein said interface operates on a mobile computing device.

5. The system of claim 1, wherein said eye gesture comprise one or more of upward gesture, downward gesture, sideways gesture, diagonal gesture and straight ahead gesture relative to the eye socket.

6. A communication method, comprising:
   audibly presenting a first set of communication options to a user, each of the first set of communication options identifying a specific eye gesture for selecting a respective communication option;
   capturing, with at least one camera images of the user's eye and eye socket of the user, said capturing is performed by a camera being attached to a head gear worn by the user such that it is directed toward the face of the user;
   dividing the eye image into at least two sections;
   determining a location of an eye pupil in one of at least two sections of said eye images;
   determining a specific eye gesture of the user based on the location of the eye pupil;
   and
   providing at least one instruction to execute according to a first communication option from a first set of communication options based on the determined specific eye gesture as corresponding to the first communication option.

7. The method of claim 6, further comprising illuminating the eye of the user with at least one light source and capturing said image with a camera are coupled to a wearable head gear worn by the user.

8. The method of claim 6, wherein said eye gesture comprises one or more of upward gesture, downward gesture, sideways gesture, diagonal gesture and straight ahead gesture relative to the eye socket.

9. An eye-based communication system, for enabling a user to communicate, comprising:
   at least one camera for capturing consecutive images of the user's eye and eye socket, the at least one camera attachable to a head gear worn by the user such that it is directed toward the face of the user; and
   a processor, communicatively coupled with said at least one camera, said processor is configured to:
      cause a speaker to audibly provide a first set of communication options to the user, each of the first set of communication options identifying a specific eye gesture for selecting a respective communication option;
      divide the image unto at least two sections;
      receive and process data representative of said images to determine a location of an eye pupil of the user in one of at least two sections of said images;
      determine a specific eye gesture of the user based on said location;
      provide at least one instruction to execute according to a first communication option from a first set of communication options based on the determined specific eye gesture as corresponding to the first communication option.

10. The system of claim 9, wherein said setting a reference comprises building a reference point coordinate system relative to the center of said grid.

11. The system of claim 9, further comprising at least one light source, optionally comprising a light emitting diode (LED), configured to illuminate the eye of the user.

12. The system of claim 11, wherein said light source comprises an infrared (IR) light source, and wherein said at least one camera is configured to detect IR light reflected from the eye.

13. The system of claim 11, wherein at least one of said light source and said at least one camera, are coupled with a wearable head gear worn by the user or wherein said interface operates on a mobile computing device.

14. The system of claim 9, wherein said eye gesture comprise one or more of upward gesture, downward gesture, sideways gesture, diagonal gesture and straight ahead gesture relative to the eye socket.

15. A communication method, comprising:
audibly presenting a first set of communication options to a user, each of the first set of communication options identifying a specific eye gesture for selecting a respective communication option;
capturing, with at least one camera, images of the user's eye and eye socket, wherein said capturing is performed by a camera being attached to a head gear worn by the user such that it is directed toward the face of the user;
dividing the eye image into at least two sections;
setting a reference point as the center of a 2D grid within said images;
determining a location of the user's eye pupil in one of at least two sections of said image;
determining a specific eye gesture of the user based on the pupil's location as corresponding to the first communication option;
providing at least one instruction to execute according to a first communication option from a first set of communication options based on the determined specific eye gesture as corresponding to the first communication option.

16. The method of claim 15, further comprising illuminating the eye of the user with at least one light source and capturing said image with a camera are coupled to a wearable head gear worn by the user.

17. The method of claim 15, wherein said eye gesture comprise one or more of upward gesture, downward gesture, sideways gesture, diagonal gesture and straight ahead gesture relative to the eye socket.

18. The method of claim 15, comprising building a reference point coordinate system relative to the center of said grid without determining the particular spatial coordinates the user is looking at in relation to a display.

19. An eye-based communication system, for enabling a user to communicate, comprising:
at least one camera for capturing images of the user's eye and eye socket; and
a processor, communicatively coupled with said at least one camera, said processor is configured to:
cause a speaker to audibly provide a first set of communication options to the user, each of the first set of communication options identifying a specific eye gesture for selecting a respective communication option;
receive and process data representative of said images to determine a a specific eye gesture of the user based thereon;
and
provide at least one instruction to execute according to a first communication option from a first set of communication options based on the determined specific eye gesture as corresponding to the first communication option.

20. A communication method, comprising:
audibly presenting a first set of communication options to a user, each of the first set of communication options identifying a specific eye gesture for selecting a respective communication option;
capturing, with at least one camera, images of the user's eye and eye socket;
processing data representative of said images to determine a specific eye gesture of the user as corresponding to the first communication option;
providing at least one instructions to execute according to a first communication option from a first set of communication options based on the determined specific eye gesture as corresponding to the first communication option.

* * * * *